United States Patent [19]

Nojima et al.

[11] Patent Number: 4,775,758
[45] Date of Patent: Oct. 4, 1988

[54] PHOSPHOLIPIDS

[75] Inventors: Shoshichi Nojima, Tokyo; Hiroaki Nomura; Susumu Tsushima, both of Osaka, all of Japan

[73] Assignee: Takeda Chemical Industries, Ltd., Osaka, Japan

[21] Appl. No.: 924,129

[22] Filed: Oct. 28, 1986

Related U.S. Application Data

[63] Continuation of Ser. No. 659,929, Oct. 11, 1984, abandoned.

[30] Foreign Application Priority Data

Oct. 11, 1983 [JP] Japan .................. 58-190348

[51] Int. Cl.$^4$ .............. C07F 9/65; C07F 9/10
[52] U.S. Cl. ...................... 546/22; 548/112; 558/169
[58] Field of Search ............ 558/169; 546/22; 548/112

[56] References Cited

U.S. PATENT DOCUMENTS

| | | | |
|---|---|---|---|
| 4,159,988 | 7/1979 | Eibl et al. | 558/169 |
| 4,372,949 | 2/1983 | Kodama et al. | 558/169 |
| 4,426,525 | 1/1984 | Hozumi et al. | 558/169 |

OTHER PUBLICATIONS

Tarnowski et al., "Cancer Research", 38, 339–344 (1978).

*Primary Examiner*—Anton H. Sutto
*Attorney, Agent, or Firm*—Wegner & Bretschneider

[57] ABSTRACT

Novel phospholipids, inclusive of salts thereof, of the formula

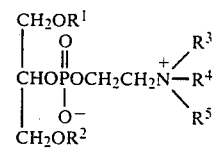

wherein
$R^1$ and $R^2$ are independently an aliphatic hydrocarbon residue containing 1 to 20 carbon atoms, with the numbers of the carbon atoms for both totalling 8 to 30, and
$R^3$, $R^4$ and $R^5$ are independently hydrogen or $C_{1-6}$ alkyl, or

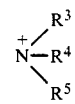

represents a cyclic ammonio group, exhibit inhibitory activity against multiplication or tumor cells and antifungal activity.

10 Claims, No Drawings

PHOSPHOLIPIDS

This application is a continuation of U.S. Ser. No. 659,929, filed Oct. 11, 1984, now abandoned.

This invention relates to phospholipids. More particularly, this invention relates to phospholipids of the formula

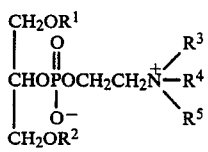 (I)

wherein
$R^1$ and $R^2$ are independently an aliphatic hydrocarbon residue containing 1 to 20 carbon atoms, with the numbers of the carbon atoms for both totalling 8 to 30, and
$R^3$, $R^4$ and $R^5$ are independently hydrogen or $C_{1-6}$ alkyl, or

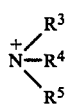

represents a cyclic ammonio group,
and salts thereof.

Phospholipids are distributed widely in organisms, existing especially as constituents of cell membranes, and are considered to serve a role in various important physiological actions through controlling the function of membranes. A typical example of the phospholipids which occur naturally is lecithin, and naturally occurring lecithins are compounds having the glycerol skeleton in the 1- and 2-positions combined with hydrophobic fatty acids by ester linkages, whereby such fatty acid comprises predominantely fatty acids of 16 and 18 carbon atoms.

The present inventors have succeeded in synthesizing the phospholipids which have not been found to occur naturally, namely the phospholipids of the formula (I) formed by introducing alkyl chains into the 1- and 3-positions of glycerol through ether linkages, and have found that they exhibit biological activities not observed with naturally occurring lecithins, and have completed this invention.

Referring to the above formula (I), the aliphatic hydrocarbon residue represented by $R^1$ and $R^2$ include straight-chain or branched aliphatic hydrocarbons of 1 to 20 carbon atoms, which may contain unsaturated bonds such as double or triple bond. As such aliphatic hydrocarbon residues, there may be mentioned, for example, straight-chain alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-octadecyl, n-nonadecyl and n-eicosanyl, branched chain alkyl groups such as 3-methylnonyl, 8-methylnonyl, 3-ethylnonyl, 3,7-dimethyloctyl and 3,5,7-trimethyloctyl; alkenyl groups such as 2-nonenyl, 4-nonenyl, 6-nonenyl, 2-decenyl, 4-decenyl, 5-decenyl, 7-decenyl, n-undecenyl, 3,7-dimethyl-2,6-octadienyl, 3,7-dimethyl-2,4,6-octatrienyl, 7-methylocta-4-enyl, 2-methylocta-2-enyl, 3,5,7-trimethyl-2,6-octadienyl, 8-tridecenyl, 8-tetradecenyl and n-dodecenyl; and alkynyl groups such as 2-nonenynyl, 4-nonenynyl, 2-decenynyl, 4-decenynyl, n-tridecanynyl and n-tetradecanynyl.

$R^1$ and $R^2$ may be any of the above-mentioned aliphatic hydrocarbon residues, only if the numbers of carbon atoms for both of them totals 8 to 30, but preferred is the case that $R^1$ and $R^2$ are the same or different and represent a $C_{4-15}$ aliphatic hydrocarbon resiude, more preferred is the case that $R^1$ and $R^2$ are the same or different and represent a $C_{7-12}$ aliphatic hydrocarbon residue and most preferred is the case that $R^1$ and $R^2$ is the same.

As the $C_{1-6}$ alkyl group represented by $R^3$, $R^4$ and $R^5$, there may be mentioned for example, methyl, ethyl, propyl, isopropyl, butyl, isobutyl, sec-butyl, tert-butyl, pentyl, hexyl, etc.

When not less than one of $R^3$, $R^4$ and $R^5$ is a hydrogen atom (for example, when $R^3$ is hydrogen), the compound (I) may in some instances be represented by the following formula:

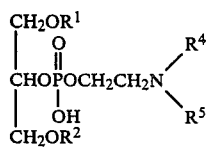 (I')

[wherein each of the symbols is as defined above].

The cyclic ammonio group as

includes, for example, pyridinio, oxazolio, thiazolio, pyridazinio, quinolinio, isoquinolinio, imidazolio and triazolo groups, and these groups may have further substituents such as $C_{1-4}$ alkyl (e.g., methyl, ethyl), hydroxy, hydroxyethyl, aminoethyl, amino (imino), carbamoyl and ureido groups. The above-mentioned cyclic ammonio group includes groups in which any two of $R^3$, $R^4$ and $R^5$ form a ring with a quaternary nitrogen atom and the remaining one is for example a hydrogen atom or lower ($C_{1-4}$) alkyl group (e.g., methyl, etc.), concretely groups in which $R^3$, $R^4$ and $R^5$, taken together with a quaternary nitrogen atom, form groups such as N-methylmorpholinio, morpholinio, N-methylpiperazinio and piperazinio groups.

The compound (I) is in some instances present in the form of salts being represented for example by the formulae:

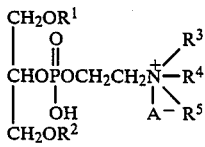 (Ia)

[wherein $A^-$ is an anion such as chlorine, bromine, iodine and tosyl ions; symbols are as defined above] and

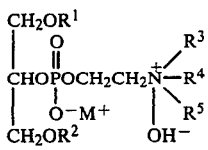 (Ib)

[wherein M+ is an alkali metal (e.g., Na, K, etc.) ion or alkaline earth metal (e.g., Ca, Mg, etc.) ion].

Conversion of the compound (I) or (I') into the compound (Ia) or (Ib) and conversion of the compound (Ia) or (Ib) into the compound (I) or (I') are easily carried out by the per se known methods.

The above compound (I) can be produced for example by the following methods:

Method A:

A compound of the formula:

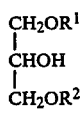 (II)

[wherein each of the symbols is as defined above] is allowed to react with a compound of the formula:

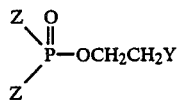 (III)

[wherein Y and Z each represents a halogen (e.g., chlorine, bromine, iodine, etc.)] to form a compound of the formula:

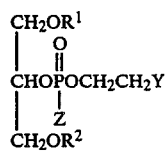 (IV)

[wherein each of the symbols is as defined above], followed by hydrolysis to give a compound of the formula:

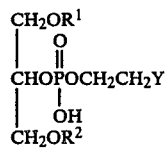 (V)

[wherein each of the symbols is as defined above].

The compound (V) can also be produced by converting a compound of the formula:

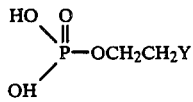 (III')

[wherein Y is as defined above] into a reactive derivative, followed by reaction with a compound (II) according to the per se known procedure.

The compound (V) is allowed to react with a compound of the formula:

 (VI)

[wherein each of the symbols is as defined above] to form the compound (I). The compound (II) can be produced by the following method through a one-step reaction in the case of $R^1$ and $R^2$ being the same or through a two-step reaction in the case of $R^1$ and $R^2$ being different.

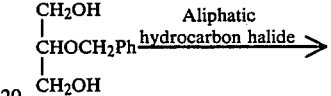

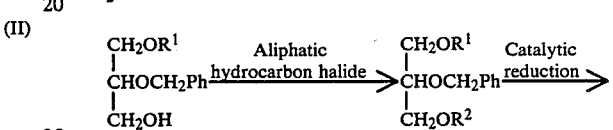

[wherein Ph is a phenyl group]

Method B:

The compound (II) can be allowed to react with a compound of the formula:

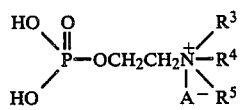 (VII)

[wherein each of the symbols is as defined above] being activated by the use of a reagent for activating phosphoric acid to produce the compound (I).

Method C:

A compound of the formula (II) is allowed to react with a phosphorylating agent such as phosphorus oxychloride, followed by hydrolysis to give a compound of the formula:

```
CH2OR¹          (VIII)
 |    O   OH
 |    ‖  /
CHOP
 |    \
 |     OH
CH2OR²
```

[wherein each of the symbols is as defined above]; subsequently, the compound (VIII) is converted into a reactive derivative with a reagent for activating phosphoric acid, followed by reaction with a compound of the formula:

```
              R³
             /
HOCH2CH2N⁺—R⁴     (IX)
         |  \
         A⁻  R⁵
```

[wherein each of the symbols is as defined above] to yield the compound (I).

While the typical methods of producing the compound (I) have been described above, a variety of other per se known reactions can be suitably applied to the production of the compound (I).

In these reactions, the reaction between the compounds (II) and (III) is conducted in accordance with the conventional procedure in an inert solvent (e.g., benzene, toluene, dichloromethane, tetrahydrofurane, etc.) in the presence or absence of a base (e.g., tertiary bases such as picoline and triethylamine). When the base is present, the reaction is allowed to proceed under ice cooling to room temperature for 2 to 8 hours. When the base is absent, heating to temperatures in the range of the boiling point of the solvent may be effected to promote the reaction. Hydrolysis of the compound (IV) is carried out by adding water to the reaction mixture of the compounds (II) and (III) after removing the solvent used in the production of the compound (IV) or as such and heating to temperatures in the range of the boiling point of the solvent for 30 minutes to 2 hours, if necessary. In order to promote the hydrolysis, an inorganic base such as sodium hydrogencarbonate, sodium carbonate and sodium hydroxide may be added to the reaction mixture in accordance with the conventional procedure.

The compound (V) is extracted with chloroform, ether, ethyl acetate, etc. The compound (V) can also be purified by silica-gel chromatography, and so forth, but can be used in the subsequent reaction with the compound (VI), without being particularly purified.

The reaction between the compounds (V) and (VI) can be conducted in an inert solvent (e.g., benzene, toluene, tetrahydrofurane, etc.) or while using the compound (VI) itself as a solvent. The reaction is carried out at a temperature ranging from room temperature to the boiling point of the solvent, but may be desirably carried out in a sealed vessel, when the compound (VI) is a low-boiling compound (e.g., tirmethylamine, dimethylamine, etc.). The object compound (I) can be purified by means of the per se known method such as silica gel chromatography, ion exchange resins, recrystallization and reprecipitation.

Conversion into reactive derivatives of the phosphoric acid derivatives such as the compound (III') in Method A, the compound (VII) in Method B and the compound (VIII) in Method C can be conducted by means of the per se known method. As such known method, by way of example, there may be mentioned a method which comprises reacting the phosphoric acid derivative with phosphorus pentachloride to form the phosphorus chloride and a method which involves the activation with the per se known condensing reagent (e.g., 2,4,6-trimethylbenzenesulfonyl chloride, 8-quinolinesulfonyl chloride, 2,4,6-isopropylbenzenesulfonylimidazolide, 2,4,6-trimethylbenzenesulfonyl tetrazolide, dicyclohexylcarbodiimide, etc.). In these methods, if the group

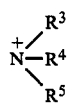

is liable to under reaction with the activating reagent or phosphoric acid derivative, the reaction can be conducted after the protection with use of the per se known protecting method, followed by removal of the protective group after the completion of the reaction to produce the object compound. For example, the compound (VII) employed in Method B is allowed to undergo reaction as a compound of the formula:

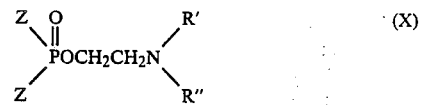

[wherein Z is as defined above; either of R' and R" is —COOCH$_2$C$_6$H$_5$—COOC$_6$H$_5$, —CHO, —COCF$_3$, —Si(CH$_3$)$_3$ or —C(C$_6$H$_5$)$_3$ and the other is R$^3$, or R' and R" undergo ring closure to represent succinimide or phthalimide], and after the treatment with water, the deprotection reaction is carried out by the suitable known method to form, out of the compounds (I), a compound of the formula:

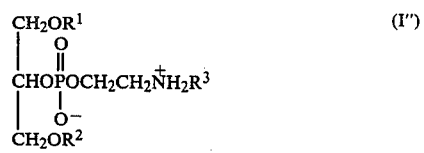

[wherein R$^1$, R$^2$ and R$^3$ are as defined above].

With reference to the compound of the formula (I) where R$^1$ and R$^2$ are different, there exist two kinds of stereoisomers having the R- and S-configurations, and these individual stereoisomers and a mixture thereof are included in the present invention.

The present inventors have succeeded in the synthesis of the compounds of the formula (I), and have found that they possess particularly excellent antitumor action and also exhibit antifungal action.

The pharmacological action characteristic of the compounds (I) will be described in detail in the following.

The compounds (I), besides possessing direct toxicity against cancer cells, exhibit host-mediated antitumor effect. As being shown in Test Examples 1 and 2, for example, the compounds (I), in both cases of in-advance and simultaneous administration, showed the significant life span prolonging effect against the sarcoma-180 transplanted tumor in the mouse tumor system, as compared with non-treated animal group. The antitumor action of the compounds (I) to cancer-carrying hosts is thought to develop as the combination of the cytotoxic effect and host-mediated effect. Furthermore, it was found that the antitumor action of the present compounds is by far enhanced as compared with that of the corresponding 1,2-dialkylglycerophosphocholines.

It has been known that the compounds (I) of the present invention and the compound of a formula similar to (I):

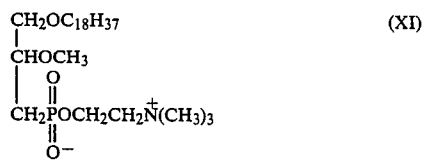

possess antineoplastic action.

However, it has also been known [Biochemical and Biophysical Research Communications, 99, 183 (1981)] that the compound (XI) has platelet aggregating action, while, on the contrary, the compounds (I) of the present invention were not found to demonstrate such activity. As shown in the experiment example, also, the compound (XI) also possesses blood-pressure lowering action, whereas the compounds of the present invention were not observed to exhibit such action. The platelet aggregation action is responsible for various circulatory disturbances, while the blood pressure lowering action itself is a serious side-effect, and these actions get to emerge as a toxicity when such compound is used as an antitumor agent. The compounds of the present invention, despite the fact that they are entirely free of such actions, exhibit life span prolonging effect equal or superior to that of the compound (XI) toward various cancer-carrying animals.

As having been described above, the compounds (I) of the present invention are of relatively low toxicity, and because of their mechanism of action described above, can be administered as an antitumor agent to warm-blooded animals (particularly mammals) afflicted with a variety of malignant tumors (e.g., leukemias, solid cancer, etc.), and produce marked life span prolonging effect.

When the compounds (I) of the present invention or their salts are used as an antitumor agent, they can be formulated into the dosage forms for oral administration such as tablets and capsules. The compounds of the present invention can be administered solely. They can also be given in combination with conventional carriers such as magnesium carbonate, magnesium stearate, talc, sugar, lactose, pectin, dextrin, starch, gelatin, tragacanth methylcellulose, sodium carboxymethylcellulose, wax being solid at ambient temperature and cocoa butter.

Diluents, flavors, dissolving agents, lubricants, suspending agents, binders, disintegrating agents, etc. may also be employed as a carrier. In addition, the compounds of the present invention, with or without other carriers added, may be filled into capsules. The proportion of the active ingredient in the above-described solid and liquid compositions, in every instances, becomes sufficient enough to provide the antitumor action at least when administered orally. Furthermore, the compounds of the present invention may be injected parenterally. In such a case, they are used, for example, in the form of sterile solutions containing aqueous sodium chloride solution or sorbitol, xylitol, glucose, etc. in sufficient quantities enough to form the isotonic solution.

The dosage varies depending upon the particular composition, route of administration, and particular subject to be treated, and the treatment is generally initiated at a level of less than the optimum dosage, with the dosage being thereafter increased until the maximum effect is achieved. In general, it is the most desirable to administer the compounds of the present invention in such a concentration as may yield the effective results without bringing about any toxic side-effect. In human being or large animals (of body weight in the range of 60 kg or more), the compounds of the formula (I) or their salts are administered at the dose level of about 20 to 100 mg/day in the case of administration through injection, and at the dose level of about 10 to 300 mg in the case of oral administration, preferably about 50 to 200 mg/day (in single dose), and may be administered in such doses being divided in the suitable number of times (e.g., twice to three times), if desired.

The compounds of the general formula (I) or their salts exhibit antifungal activity, example of which include fungicidal actions against *Trichophyton mentagrophytes, Aspergillus niger, Penicillium citrinum, Rhodotolula rubra*, etc., and are therefore useful for prophylaxis and therapy of diseases caused by these fungi. In contrast with this, these compounds hardly exhibit any activity against procaryotic cells.

The antifungal agents are formulated into preparations in accordance with the conventional method. The amount of the active ingredient is not to be limited, but the compounds of the present invention, when being for example used for the purpose of treatment of trichophytosis, are employed at the rate of about 0.01 to 70 weight % against the whole preparation, more preferably about 0.1 to 5 weight %. The antifungal agents are conveniently administered in accordance with the conventional method by applying them to affected parts once to several times a day by means such as coating and spraying.

Furthermore, the compounds (I) possess antimicrobial activity against phytopathogenic microorganisms, particularly fungi, and are useful as a fungicidal agent for agricultural use against plant diseases such as blast of rice, grey mildew and citrus black spot. The fungicidal agents for agricultural use are formulated into preparations in accordance with the conventional method, and the content of the active ingredient in such preparations, normally, is suitably in the range of 10 to 90% in the case of emulsifiable concentrate and wettable powder, in the region of 0.1 to 10% in the case of oily preparation and powder and in the range of 5 to 50% in the case of granule. The emulsifiable concentrate, wettable powder, etc., at the time of use, is desirably diluted suitably (for example to 50 to 5000 fold) with water and the like and sprayed. The fungicidal agents for agricultural use are applied by the per se known various application methods; in general, they may be applied at the rate in the range of 10 to 300 g as the active ingredient per 10 ares, and are desirably applied in the application concentration in the range of 10 to 1000 ppm of the active ingredient.

Embodiment examples, test examples and preparation examples are to be described below to illustrate the present invention in more particular, but it is to be understood that these will not limit the present invention.

EXAMPLE 1

1,3-Dioctyloxypropane-2-yl 2-trimethylammonioethyl phosphate (1) 1,3-Dioctyl-2-benzylglycerin In a mixed solution consisting of 50 ml of DMSO and 30 ml of THF were dissolved 3.64 g (20 mmole) of 2-benzylglycerin and 9.26 g (48 mmole) of octyl bromide, and 8.96 g (160 mmole) of powdered potassium hydroxide was added to the solution, followed by vigorous stirring. Two hours later, the reaction solution was poured in cold water, and the mixture was extracted with n-hexane. The extract was washed with water, dried and concentrated, followed by purification by silica-gel chromatography (eluent: n-hexane-ethyl acetate, 20:1) to give 6.22 g (77%) of the desired compound as colorless liquid.

IR (film) cm$^{-1}$: 3060, 3030, 2930, 2860, 1500, 1465, 1455, 1380, 1115, 735, 695.

NMR (90 MHz, CDCl$_3$)δ: 0.87(6H, t), 1.25(24H, m), 3.35-3.53(8H, m), 3.68(1H, m), 4.70(2H, s), 7.32(5H, m).

(2) 1,3-Dioctylglycerin

In a mixed solution consisting of 60 ml of acetic acid and 20 ml of ethanol was dissolved 6.2 g of the above benzyl derivative, and catalytic reduction was carried out under a stream of hydrogen gas with use of 5% palladium carbon. After the completion of the reaction, the solvent was distilled off, and the residue was purified by silica-gel chromatography to yield 4.47 g (93%) of the desired compound as a colorless liquid.

IR (film) cm$^{-1}$: 3455, 2930, 2860, 1465, 1380, 1115.

NMR (90 MHz, CDCl$_3$)δ: 0.87(6H, t), 1.27(20H, m), 1.57(4H, m), 2.43(1H, d, OH), 3.3-3.6(8H, m), 3.93(1H, m).

(3) 1,3-Dioctyloxypropane-2-yl 2-trimethylammonioethyl phosphate

In 40 ml of benzene was dissolved 4.47 g (14.1 mmole) of the above alcohol derivative, and 5.9 g (24.2 mmole) of 2-bromoethyl phosphorodichloridate and then 1.92 ml (24.2 mmole) of pyridine were added dropwise to the solution under ice-cooling. After the stirring at room temperature for 3 hours, 30 ml of water was added to the reaction solution, followed by vigorous stirring at 90° C. for 45 minutes. After cooling, the solvent was distilled off, and the residue was dissolved in ether. The solution was washed with water, and concentrated to dryness. The residue was dissolved in 40 ml of toluene containing 8 g of trimethylamine, and the solution was stirred for 3 days. The reaction solution was concentrated to dryness, and the residue was purified by silica-gel chromatography (eluent: firstly methanol and secondly chloroform-methanol-water, 65:25:4) to give 3.70 g (54%) of the desired compound as a colorless solid.

IR (KBr) cm$^{-1}$: 3420, 2960, 2940, 2865, 1485, 1470, 1380, 1240, 1100, 970, 800.

NMR (90 MHz, CDCl$_3$)δ: 0.87(6H, t), 1.25(24H, m), 3.35(9H, s), 3.4-3.6(8H, m), 3.80(2H, m), 4.31(3H, br)

TLC: Rf=0.20 (CHCl$_3$—CH$_3$OH—H$_2$O, 65:25:4)

Elemental analysis, for C$_{24}$H$_{52}$NO$_6$P.0.25H$_2$O: Calcd.: C, 59.29; H, 10.88; N, 2.88; P, 6.37. Found: C, 59.32; H, 11.11; N, 2.95; P, 6.46.

EXAMPLE 2

1,3-Dioctyloxypropane-2-yl 2-aminoethyl phosphate

In 32 ml of toluene was dissolved 5.06 g (16.0 mmole) of the glycerin derivative obtained in Example 1-2), and 6.58 g (27.2 mmole) of 2-bromoethyl phosphorodichloridate and then 2.15 g (27.2 mmole) of pyridine were added dropwise to the solution, followed by stirring at room temperature for 4 hours. The reaction solution was concentrated to dryness under reduced pressure, and 50 ml of water added to the residue. The mixture was heated under reflux for 45 minutes, with vigorous stirring, then cooled and extracted with 50 ml of ether. The ether layer was concentrated to dryness to give 8.055 g (yield of 100%) of the bromide derivative. The bromide derivative (2.685 g, 5.33 mmole) and 4.2 g (21.32 mmole) of dibenzylamine were dissolved in 10 ml of toluene, and the solution was allowed to stand at room temperature for 2 days. The reaction solution was concentrated to dryness under reduced pressure, and the residue was purified by chromatography on a silica gel column (25 g) (eluent, CHCl$_3$—CH$_3$OH (95:5), CHCl$_3$—CH$_3$OH (65:25)). The product, without being further purified, was dissolved in 100 ml of 70% acetic acid, and the solution was vigorously stirred in the presence of palladium carbon (2 g) in a stream of hydrogen gas. The insoluble matter was filtered off, and the filtrate was concentrated to dryness under reduced pressure. The residue was purified by chromatography on silica gel (25 g) (eluent: firstly CHCl$_3$—CH$_3$OH (95:5), secondly CHCl$_3$—CH$_3$OH (65:25)) to give the desired compound as a colorless powder. Yield of 1.5 g.

Thin-layer chromatography [silica gel, CHCl$_3$, CH$_3$OH, H$_2$O (65:25:4)] Rf=0.33.

IR (film) cm$^{-1}$: 3400, 2930, 2850, 1630, 1465, 1225, 1080, 1025, 900, 810.

NMR (60 MHz, CDCl$_3$)δ: 0.88(6H), 1.25(24H), 3.0-4.0(12H), 4.0-4.8(4H).

Elemental analysis, for C$_{21}$H$_{46}$NO$_6$P—0.8H$_2$O: Calcd.: C, 56.82; H, 8.54; N, 3.16; P, 6.98. Found: C, 56.84; H, 8.64; N, 3.18; P, 7.05.

EXAMPLE 3

1,3-Dioctyloxypropane-2-yl 2-thiazolioethyl phosphate

In 5 ml of toluene were dissolved 2.685 g (5.33 mmole) of the bromide derivative obtained in Example 2 and 3.0 g (35.2 mmole) of thiazole, and the solution was stirred at 70° C. for 2 days. The reaction solution was concentrated to dryness under reduced pressure, and the residue was purified by chromatography on a silica gel column (25 g) (eluent: firstly CHCl$_3$—MeOH (95:5), secondly CHCl$_3$—MeOH (65:25)) to give 0.8 g (yield of 28.6%) of a yellowish solid substance.

Thin-layer chromatography [silica gel, CHCl$_3$, MeOH, H$_2$O (65:25:4)] Rf=0.65 as a single spot.

IR (film) cm$^{-1}$: 3350, 3100, 2930, 2850, 1630, 1550, 1465, 1235, 1100, 1020.

Elemental analysis, for C$_{24}$H$_{46}$NO$_6$PS—H$_2$O: Calcd.: C, 54.84, H, 9.20; N, 2.66; P, 5.89. Found: C, 54.92; H, 9.50; N, 2.65; P, 5.78.

EXAMPLE 4

1,3-Didecyloxypropane-2-yl 2-trimethylammonioethyl phosphate (1) 1,3-Didecyl-2-benzylglycerin By treating 4.55 g (25 mmole) of 2-benzylglycerin and 11.76 g (50 mmole) of decyl bromide according to the method described in Example 1-(1) and (2), there was obtained 6.9 g of 1,3-didecyl-2-benzylgrlycerin, which was furthermore subjected to removal of benzyl through catalytic reduction to give 4.8 g (yield of 51.5%) of 1,3-didecylglycerin.

IR (film) cm$^{-1}$: 3455, 2930, 2860, 1465, 1380, 1115.

(2) 1,3-Didecyloxypropane-2-yl 2-trimethylammonioethyl phosphate

In 25 ml of toluene were dissolved 4.8 g (12.88 mmole) of the above glycerin derivative and 5.45 g (22.53 mM) of 2-bromoethyl phosphorodichloridate, and 1.78 g (22.53 mmole) of pyridine was added dropwise to the solution, followed by stirring at room temperature for 3 hours and treatment in accordance with the method described in Example 1-3) to give 7.2 g (yield of 100%) of the desired bromide derivative as a colorless solid substance. The bromide derivative (2.4 g, 4.29 mmole) was dissolved in 25 ml of 20% trimethylamine-toluene solution, and the solution was allowed to stand at room temperature for 2 days. The reaction solution was concentrated to dryness under reduced pressure, and the residue was purified by chromatography on a silica gel column (20 g) (eluent: CHCl$_3$—MeOH—H$_2$O (65:25:2)) to give the desired compound as a colorless solid substance. Yield of 1.7 g (yield of 92.3%).

Thin-layer chromatography [silica gel, CHCl₃, CH₃OH, H₂O (65:25:4)] Rf=0.16 as a single spot.

EXAMPLE 5

1,3-Didecyloxypropane-2-yl 2-pyridinioethyl phosphate

In 30 ml of pyridine was dissolved 2.4 g (4.29 mmole) of the bromide derivative obtained in Example 4, and the solution was stirred on a water bath of 70° C. for 3 days. The reaction solution was concentrated to dryness under reduced pressure, and the residue was purified by chromatography on a silica gel column (20 g) (eluent; CHCl₃—MeOH (65:25)) and chromatographed again under the same conditions to give 1.0 g (yield of 41.8%) of a colorless solid substance.

Thin-layer chromatography [silica gel, CHCl₃, MeOH, H₂O (65:25:4)] Rf=0.30 as a single spot.

IR (film) cm⁻¹: 3400, 2920, 2850, 1465, 1230, 1075, 1050.

NMR (60 MHz, CDCl₃)δ: 0.87(6H), 1.23(32H), 3.33(9H), 4.20(2H), 5.08(2H), 7.90(2H), 8.23(1H), 9.08(2H).

EXAMPLE 6

1,3-Didecyloxypropane-2-yl 2-dimethylaminoethyl phosphate

In 25 ml of 20% dimethylamino-toluene solution was dissolved 2.4 g (4.29 mmole) of the bromide derivative obtained in Example 4, and the solution was allowed to stand at room temperature for 2 days. The reaction solution was concentrated to dryness under reduced pressure, and the residue was purified by chromatography on a silica gel column (25 g) (eluent; CH₃OH) and by further chromatography on a silica gel column (20 g) (eluent; CHCl₃—CH₃OH—H₂O (65:25:2)) to give 2.1 g (yield of 93.5%) of a colorless solid substance.

Thin-layer chromatography [silica gel, CHCl₃, CH₃OH, H₂O (65:25:4)] Rf=0.36 as a single spot.

IR (film) cm⁻¹: 3400, 2920, 2850, 1650, 1465, 1230, 1080, 1060(sh), 940, 800 760.

NMR (60 MHz, CDCl₃)δ: 0.87(6H), 1.27(32H), 2.78(6H), 2.94-3.65(9H), 4.21(4H).

Elemental analysis, for C₂₇H₅₈NO₆P—0.8H₂O: Calcd.: C, 60.26; H, 11.46; N, 2.60; P, 5.76. Found: C, 60.46; H, 10.75; N, 2.59; P, 5.70.

EXAMPLE 7

1,3-Didodecyloxypropane-2-yl 2-trimethylammonioethyl phosphate (1) 1,3-Didodecylglycerin According to the method described in Example 1-(1), 12.46 g (50 mmole) of dodecy bromide and 4.55 g (25 mmole) of 2-benzylglycerol were treated, followed by catalytic reduction in accordance with the method described in Example 1-(2) to give 5.2 g of a colorless solid substance (Yield of 45.5%).

NMR (60 MHz, CDCl₃)δ: 0.87(6H), 1.23(40H), 2.20(1H), 3.17-3.53(8H), 3.80(1H).

(2) 1,3-Didodecyloxypropane-2-yl 2-dimethylaminoethyl phosphate

In 22 ml of toluene were 5.0 g (10.96 mmole) of the above glycerol derivative and 4.51 g (18.62 mmole) of 2-bromoethyl phosphorodichloridate, and 1.47 g (18.62 mmole) of pyridine was added dropwise to the solution, followed by stirring at room temperature for 4 hours.

The reaction solution was concentrated to dryness under reduced pressure, and the residue was suspended in 100 ml of water. The suspension was heated under reflux for 45 minutes with vigorous stirring, then cooled and extracted with 100 ml of ether. The ether layer was concentrated to dryness under reduced pressure to give the bromide derivative. Yield of 6.75 g (Yield of 100%).

In 50 ml of 20% dimethylamino-toluene solution was dissolved 3.38 g (5.48 mmole) of the bromide derivative, and after being allowed to stand at room temperature for 2 days, the solution was treated in accordance with the method described in Example 6 to give 2.3 g (yield of 72.4%) of a colorless powder.

Thin-layer chromatography [silica gel, CHCl₃, CH₃OH, H₂O (65:24:4)] Rf=0.42 as a single spot.

IR (film) cm⁻¹: 3420, 2920, 2850, 1465, 1230, 1090, 1070, 810.

NMR (60 MHz, CDCl₃)δ: 0.87(6H), 2.77(6H), 2.93-3.66(9H), 4.20(4H).

Elemental analysis, for C₃₁H₆₆NO₆P: Calcd.: C, 64.21; H, 11.47; N, 2.42; P, 5.34. Found: C, 64.45; H, 11.61; N, 2.44; P, 5.35.

EXAMPLE 8

1,3-Didodecyloxypropane-2-yl 2-trimethylammonioethyl phosphate

In 35 ml of 20% trimethylamine-toluene solution was dissolved in 3.38 g (5.48 mmole) of the bromide derivative obtained in Example 7, and the solution was allowed to stand at room temperature for 3 days. The reaction solution was concentrated to dryness under reduced pressure, and the residue was treated in accordance with the method described in Example 1-3) to give 2.2 g (yield of 67.6%) of the desired compound as a colorless solid substance.

Thin-layer chromatography [silica gel, CHCl₃, CH₃OH, H₂O (65:25:4)] Rf=0.27 as a single spot.

IR (film) cm⁻¹: 3400, 2920, 2850, 1465, 1230, 1090, 1060, 970.

NMR (60 MHz, CDCl₃)δ: 0.85(6H), 1.23(40H), 3.28(9H), 3.2-3.83(9H), 4.28(4H).

Elemental analysis, for C₃₂H₆₈NO₆P—0.8H₂O: Calcd.: C, 63.19; H, 11.58; N, 2.30; P, 5.09. Found: C, 63.25; H, 11.50; N, 2.08; P, 5.00.

EXAMPLE 9

(1) 1,3-Dinonylglycerol

In 50 ml of 1N potassium t-butoxide were heated under reflux for 18 hours 2.73 g (15 mmole) of 2-benzylglycerol and 6.22 g (30 mmole) of n-nonyl bromide. The reaction solution was concentrated to dryness under reduced pressure, and the residue was suspended in 50 ml of water. The suspension was neutralized and extracted with 35 ml dichloromethane. The organic layer was concentrated to dryness under reduced pressure, and the residue was dissolved in 50 ml of 80% acetic acid, followed by stirring in the presence of palladium carbon (320 mg) in a stream of hydrogen gas for 16 hours. The insoluble matter was filtered off, and the filtrate was concentrated to dryness under reduced pressure. The residue was purified by chromatography on silica gel (30 g) (eluent: n-hexane-ethyl acetate (19:1)) to give 2.1 g (yield of 40.6%) of a colorless oily substance.

(2) 1,3-Dinonyloxypropane-2-yl 2-trimethylammonioethyl phosphate

In 14 ml of toluene were dissolved 2.1 g (6.09 mmole) of the 2-hydroxy derivative obtained in Example 9-(1) and 2.51 g (10.36 mmole) of 2-bromoethyl phosphorodichloridate, followed by stirring at room temperature for 3 hours. The reaction solution was concentrated to dryness under reduced pressure, and the residue was suspended in 20 ml of water. The suspension was heated under reflux for 45 minutes, cooled and extracted with 40 ml of ether. The organic layer was concentrated to dryness under reduced pressure, and the residue was dissolved in 20 ml of 20% trimethylamine-toluene solution, and the resulting reaction solution was allowed to stand at room temperature for 2 days and concentrated to dryness under reduced pressure. The residue was purified by chromatography on a silica gel column (30 g) (eluent: methanol) and by further chromatography on a silica gel column (25 g) (eluent; chloroform, methanol, water (65:25:4)) to give 1.76 g (yield of 51.3%) of a colorless solid substance.

Thin-layer chromatography [silica gel, $CHCl_3$, $CH_3OH$, $H_2O$, (65:25:4)] Rf=0.25 (as a single spot).

IR (film) $cm^{-1}$: 3400, 2930, 2850, 1650, 1490, 1465, 1230, 1090, 1060(sh), 975.

NMR (60 MHz, $CDCl_3$)δ: 0.88(6H), 1.28(28H), 3.43(9H), 3.4–3.7(8H), 3.93(1H), 4.33(4H).

Elemental analysis, for $C_{26}H_{56}NO_6P—3H_2O$ (563.75): Calcd.: C, 55.39; H, 11.08; N, 2.48; P, 5.49. Found: C, 55.25; H, 11.02; N, 2.61; P, 5.34.

EXAMPLE 10

(1) 1,3-Diheptylglycerol

In 50 ml of 80% acetic acid was dissolved 3.1 g (8.19 mmole) of 1,3-diheptyl-2-benzylglycerol, and the solution was stirred in the presence of 310 mg of palladium carbon in a stream of hydrogen gas overnight. The insoluble matter was filtered off from the reaction solution, and the residue was purified by chromatography on a silica gel column (30 g) (eluent, n-hexane, ethyl acetate (19:1)) to give 2.36 g (yield of 100%) of a colorless oily substance.

Thin-layer chromatography [silica gel, n-hexane, ethyl acetate (9:1)] Rf=0.24 as a single spot.

(2) 1,3-Diheptyloxypropane-2-yl 2-trimethylammonioethyl phosphate

In 16 ml of toluene were dissolved 2.36 g (8.19 mmole) of the 2-hydroxy derivative obtained in Example 10-(1) and 3.36 g (13.93 mmole) of 2-bromoethyl phosphorodichloridate, and 1.1 g (13.93 mmole) of pyridine was added dropwise to the solution, followed by stirring at room temperature for 3 hours. The reaction solution was concentrated to dryness under reduced pressure, and the residue was suspended in 30 ml of water. The suspension was heated under reflux for 45 minutes, then cooled and extracted with 50 ml of ether. The ether layer was concentrated to dryness under reduced pressure, and the residue was dissolved in 30 ml of 20% trimethylamine-toluene solution. The reaction solution was allowed to stand at room temperature for 2 days and concentrated to dryness under reduced pressure, and the residue was purified by chromatography on silica gel (30 g) (eluent; methanol) and by further chromatography on silica gel (30 g) (eluent, chloroform, methanol, water (65:25:4)) to give 1.5 g (yield of 38.9%) of a colorless solid substance.

Thin-layer chromatography [silica gel, $CHCl_3$, $CH_3OH$, $H_2O$ (65:25:4)] Rf=0.25 (as a single spot).

IR (film) $cm^{-1}$: 3400, 2930, 2850, 1650, 1490, 1230, 1090, 1060(sh), 975.

Elemental analysis, for $C_{22}H_{48}NO_6P—H_2O$(471.61): Calcd.: C, 56.03; H, 10.69; N, 2.97; P, 6.57. Found: C, 55.97; H, 10.71; N, 3.00; P, 6.78.

TEST EXAMPLE 1

Antitumor activity (pre-administration) of 1,3-dioctyloxypropane-2-yl 2-trimethylammonioethyl phosphate (Example 1)

A 1 mg/mouse of the compound of Example 1 was admixed with physiological saline, and administered intraperitoneally to ICR mice (a group consisting of 5 mice). Four days later, $1 \times 10^5$ sarcoma 180 cells per mouse was transplanted intraperitoneally to each of the mice. The rate of life span prolongation against the control group not given the drug compound (T/C) was found to be 225.

TEST EXAMPLE 2

Antitumor activity (simultaneous administration) of 1,3-dioctyloxypropane-2-yl 2-trimethylammonioethyl phosphate (Example 1)

Sarcoma 180 cells ($1 \times 10^5$ cells per mouse) was transplanted intraperitoneally to ICR mice (a group consisting of 5 mice). Subsequently, the compound of Example 1 (1 mg/mouse) was dissolved in physiological saline, and administered intraperitoneally to each of the mice. In the group given the drug compound, two mice survived 60 days, and the rate of life prolongation against the control group not given the drug compound was 458.

The same test for the purpose of comparison with 2,3-dioctyloxypropyl 2-trimethylammonioethyl phosphate revealed 195 of the rate of life prolongation.

TEST EXAMPLE 3

Antitumor activity of 1,3-dioctyloxypropane-2-yl 2-trimethylammonioethyl phosphate (Example 1)

Sarcoma 180 cells ($1 \times 10^6$ cells) were transplanted subcutaneously to each of ICR mice (a group consisting of 5 mice). The compound of Example 1 was administered intraperitoneally to the mice at the single dose rate of 0.2 mg/mouse 13 times over the period of from the 2nd day to the 20th day. On the 21th day, the mice were anatomized, and the weight of tumors was measured. Comparison between the treated group and the control group not given the drug compound for the weight of tumors indicated 54% of the growth inhibition rate of tumor.

TEST EXAMPLE 4

Antitumor activity of 1,3-dioctyloxypropane-2-yl 2-trimethylammonioethyl phosphate (Example 1)

Sarcoma 180 cells ($1 \times 10^6$ cells) were transplanted subcutaneously to each of ICR mice (a group consisting of 5 mice). The compound of Example 1 was injected intravenously to the mice at the single dose rate of 0.06 mg/mouse 9 times over the period of from the 7th day after the transplantation to the 20th day. On the 21th day, the mice were anatomized, and the weight of tumors was measured. Comparison between the treated group and the control group not given the drug compound for the weight of tumors indicated 52% of the growth inhibition rate of tumor.

TEST EXAMPLE 5

Antitumor activity of 1,3-dioctyloxypropane-2-yl 2-thiazolioethyl phosphate (Example 3)

P 388 leukemia cells ($1 \times 10^6$ cells) were mixed with 0.1 g of the compound of Example 3, and transplanted subcutaneously to each of $CDF_1$ mice (a group consisting of 5 mice). On the 10th day, the weight of tumors was measured, and comparison with the control group not given the drug compound indicated that the drug compound shows 83% of the growth inhibition rate of tumor.

TEST EXAMPLE 6

Antitumor activity of 1,3-dinonyloxypropane-2-yl 2-trimethylammonioethyl phosphate (Example 9)

Meth A cells ($1 \times 10^6$ cells per mouse) were transplanted subcutaneously to $CDF_1$ mice (a group consisting of 5 mice). On the other hand, a solution of 0.25 mg/mouse of the compound of Example 9 in 0.05 ml of physiological saline was given to each of the mice on the portion transplanted with the cells once a day for 4 consecutive days from the 1st day following the transplantation. Ten days later, the tumor tissues were removed, and the weight of tumors was measured. Comparison with the control group for the weight of tumors indicated 76% of the growth inhibition rate of tumor.

TEST EXAMPLE 7

Antitumor activity of 1,3-diheptyloxypropane-2-yl 2-trimethylammonioethyl phosphate (Example 10)

Sarcoma 180 cells ($4 \times 10^5$ cells per mouse) were transplanted intraperitoneally to ICR mice (a group consisting of 5 mice). The compound of Example 10 was administered intraperitoneally to the mice at the single dose rate of 25 mg/kg for 9 consecutive days from the day following transplantation. The rate of life span prolongation against the control group not given the drug compound (T/C) was found to be 295.

TEST EXAMPLE 8

Antifungal action of 1,3-dioctyloxypropane-2-yl 2-trimethylammonioethyl phosphate (Example 1)

Using typical fungi, the minimal inhibition concentrations (MIC) were determined with the compound of Example 1 by the serial dilution technique on a 1% glucose bouillon agar culture medium.

| Name of fungi | MIC ($\mu$g/ml) |
| --- | --- |
| *Piricularia oryzae* | 6.25 |
| *Botrytis cinerea* | 3.12 |
| *Diaporthe citri* | 6.25 |
| *Elsinoe fawcetti* | 3.12 |
| *Helminthosporium oryzae* | 3.12 |
| *Cercospora beticola* | 6.25 |
| *Penicilium citrinum* | 12.5 |
| *Cladosporium herbarum* | 6.25 |
| *Mucor spinescens* | 12.5 |
| *Saccharomyces cerevisiae* | 25 |

TEST EXAMPLE 9

Action on blood platelets

Testing procedures and results

With use of an injection syringe containing 3.15% citric acid (in the proportion of 1 against 9 of blood) as an anticoagulant, a blood sample was taken from a male rabbit and centrifuged at 1000 rpm at room temperature for 10 minutes to give a platelet rich plasma (PRP). The PRP was furthermore centrifuged at 1400 rpm for 15 minutes to give a platelet pellet, which was then suspended in $Ca^{++}$ free Tyrode to prepare a washed PRP. The washed PRP (250 $\mu$l) was stirred at 37° C. for for 2 minutes, and then 25 $\mu$l of 0.2 to 0.5 mM $Ca^{++}$ solution was added, followed by stirring for 30 seconds. Subsequently, there was added a test drug compound in such an amount as the concentration of $3 \times 10^{-5}$M. Platelet aggregation was measured by an aggregation meter (produced by Rika Denki Co. of Japan). The control compound (XI) showed 46% to 63% of aggregation, whereas the compounds of Examples 1 to 10 each caused no aggregation.

TEST EXAMPLE 10

Blood-pressure lowering action

Male 7-week aged Sprague-Dawley rats (weighing 200 to 290 g) were anesthetized by intraperitoneal administration of 60 mg/kg of pentobarbital sodium, and the left carotids (for the measurement of blood pressure) and left femoral veins (for the intravenous administration) were cannulated. Administration of 300 $\mu$g/kg of the control compound (XI) was found to result in a blood pressure lowering of 43 to 75 mmHg, whereas no blood pressure lowering action was observed with every compounds as shown in Examples 1 to 10.

TEST EXAMPLE 11

Antitumor activity of 1,3-Dinonyloxypropane-2-yl 2-trimethylammonioethyl phosphate (Example 9)

ICR mice (5 animals per group) were intraperitoneally inoculated with $1 \times 10^5$ sarcoma 180 cells per mouse. Thereafter, a solution of the compound of Example 9 in physiological saline was administered in a dose of 0.33 mg/mouse three times, namely at hour 1, day 1 and day 2. The life span prolonging ratio as compared with the control (no drug treatment) group was 198, and 1 animal survived on day 60.

TEST EXAMPLE 12

Antitumor activity of the compound of Example 9

The compound of Example 9 was intraperitoneally administered to C3H/He mice (5 animals per group) in a dose of 0.25 mg/mouse for 4 consecutive days.

On the 5th day, $1 \times 10^4$ MM46 cells were intraperitoneally inoculated into each mouse, and the compound of Example 9 was again administered intraperitoneally to the mice in a dose of 0.25 mg/mouse for 4 days starting from day 1 after inoculation.

The mice in the control group all died within 19 days after tumor implantation, whereas, in the drug-treated group, 3 animals survived on day 60.

PREPARATION EXAMPLE 1

In 1.0 l of distilled water is dissolved 80 g of 1,3-dioctyloxypropane-2-yl 2-trimethylammonioethyl phosphate, and the solution was sterile-filtered, distributed in 1 ml portions into 1000 vials under sterile conditions, and lyophilized, followed by tight closing of the vials.

On the other hand, 2 l of distilled water for injection containing 100 g of xylitol or mannitol is distributed in 2 ml portions into ampoules for injection, which are then sealed to prepare 1000 injections.

The powder contained in the above-mentioned one vial, at the time of use, is dissolved in the xylitol solution (or mannitol solution) for injection, and used for administration.

PREPARATION EXAMPLE 2

Tablet:

| | |
|---|---|
| (1) 1,3-Dioctyloxypropane-2-yl 2-trimethyl-ammonioethyl phosphate | 100 mg |
| (2) Lactose | 200 mg |
| (3) Corn starch | 51 mg |
| (4) Hydroxypropylcellulose | 9 mg |

The above ingredients in the amounts indicated for one tablet are mixed and granulated by the conventional method. The granules are mixed with corn starch (8 mg) and magnesium stearate (2 mg), and the mixture is compressed into a tablet

PREPARATION EXAMPLE 3

The tablet of the above Preparation Example 2 is provided with a coating by use of an acetone-ethanol (4:6) mixed solution having hydroxypropylmethyl methylcellulose phthalate (14 mg) and castor oil (1 mg) (the amounts indicated for one tablet) dissolved therein to a concentration of 7% to form an enteric-coated tablet.

We claim:

1. A compound of the formula

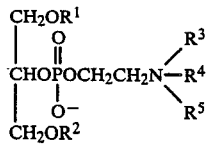

wherein each of $R^1$ and $R^2$ is independently selected from an aliphatic hydrocarbon group of 1 to 20 carbon atoms, the total number of carbon atoms of both groups being from 8 to 30; and each of $R^3$, $R^4$ and $R^5$ is independently hydrogen or $C_{1-6}$ alkyl or

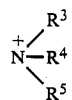

is pyridinio or thiazolio.

2. A compound according to claim 1, wherein the aliphatic hydrocarbon residue is alkyl.

3. A compound according to claim 1, wherein $R^1$ and $R^2$ are the same and represent a $C_{4-15}$ aliphatic hydrocarbon residue.

4. A compound according to claim 1, wherein $R^1$ and $R^2$ are the same and represent a $C_{7-12}$ aliphatic hydrocarbon residue.

5. A compound according to claim 1, wherein $R^1$ and $R^2$ are the same and represent $C_{7-12}$ alkyl.

6. A compound according to claim 1, wherein

represents thiazolio.

7. A compound according to claim 1, wherein

represents pyridinio.

8. The compound according to claim 1, which is 1,3-dioctyloxypropane-2-yl 2-trimethylammonioethyl phosphate.

9. The compound according to claim 1, which is 1,3-dioctyloxypropane-2-yl 2-thiazolioethyl phosphate.

10. The compound according to claim 1, which is 1,3-dinonyloxypropane-2-yl 2-trimethylammonioethyl phosphate.

* * * * *